United States Patent [19]
Lewis, Jr.

[11] Patent Number: 5,329,813
[45] Date of Patent: Jul. 19, 1994

[54] GRASP ANALYSIS APPARATUS

[76] Inventor: Royce C. Lewis, Jr., 5233 - 19th St., Lubbock, Tex. 79407

[21] Appl. No.: 965,587

[22] Filed: Oct. 23, 1992

Related U.S. Application Data

[63] Continuation of Ser. No. 599,775, Oct. 17, 1990, Pat. No. 5,157,970.

[51] Int. Cl.⁵ ............................................. A61B 5/22
[52] U.S. Cl. .................................. 73/379.03; 128/774
[58] Field of Search ........................ 73/379.02, 379.03; 128/26, 774

[56] References Cited

U.S. PATENT DOCUMENTS 5,125,270  6/1992  Kovacevic ..................... 73/379.02
5,184,628  2/1993  Shah et al. ..................... 73/379.02

FOREIGN PATENT DOCUMENTS 2153540  8/1985  United Kingdom ............. 73/379.02

Primary Examiner—Donald O. Woodriel
Attorney, Agent, or Firm—Marcus L. Bates

[57] ABSTRACT

A grasp analysis apparatus and method by which the power of grasp exerted by the human hand can be measured, and by which a determination can be made related to the maximum effort of grasp that is made during the measurement. The apparatus includes a housing having opposed walls which can be forced towards one another in proportion to the magnitude of the compressive strength exerted by the person that grasps the housing. A transducer enclosed within the housing is compressed between the movable opposed walls and provides a signal that is proportional to the magnitude of the compressive force of the grasp. The signal is converted into a measurement indicative of the magnitude of the force. A plurality of measurements taken at different locations along the fingers are plotted to reveal the true effort being made while grasping the apparatus.

14 Claims, 2 Drawing Sheets

GRASP ANALYSIS APPARATUS

REFERENCE TO RELATED APPLICATIONS

This application is a continuation of parent application Ser. No. 07/599,775 Filed Oct. 17, 1990 Entitled "GRASP ANALYSIS APPARATUS AND METHOD" Now U.S. Pat. No. 5,157,970 Issued Oct. 27, 1992.

BACKGROUND OF THE INVENTION

The human hand has a bony framework consisting of eight carpal or wrist bones arranged in two rows, five metacarpal or palm bones, and fourteen phalanxes or finger bones, all of which are held together by a complex system of ligaments that allow an amazing degree of movement to achieve grasping or comprehension. The hand includes highly coordinated muscular action, and complex nervous receptors, that senses touch, pressure, temperature and pain and further enables an object to be grasped with great force.

On the other hand, the complex arrangement of the nerves, ligaments, and bones occasionally do not function properly due to injury or disease and this disfunction often is curable by placing one's injured hand in the care of an expert who has spent a lifetime studying the human hand.

It is therefore desirable to be able to evaluate the extent of injury to one's hand in order to determine the seriousness and character of an injury. Often, for one reason or another, a person will not display the true extent of his injured hand by not making his maximum effort when the force of his grasp is being measured and thus the true extent of injury to the hand is obscured to the evaluator. Method and apparatus by which the extent that the patient making his maximum effort when his grasp is being measured is the subject of the present invention.

SUMMARY OF THE INVENTION

This invention comprehends a grasp analysis apparatus by which the power of grasp in the human hand can be measured by the provision of a hand held transducer having collapsible walls on opposed sides thereof for engagement of the fingers and the palms, whereupon increased force of grasp forces the opposed walls toward one another and the transducer generates a signal that is proportional to the magnitude of the force of the grasp.

More specifically, the grasp analysis apparatus by which the power of the grasp of the human hand can be measured includes a palm engaging part spaced from a finger engaging part and adjustably connected together whereby different selected portions of the fingers are engaged by the finger engaging part to thereby enable the force exerted by various different areas of the fingers to be accurately measured.

Still more specifically, the before mentioned grasp analysis apparatus further includes a transducer for generating a signal that is proportional to the force of the grasp and changing the signal into data which is representative of the magnitude thereof.

The above grasp analysis apparatus enables a method of evaluating the force of grasp to be carried out wherein the true force that one can exert with a hand is determined. More particularly, the method evaluates whether the true force of grasp is being exerted with the hand when one is exerting less than the maximum force he is actually capable of exerting.

The method of the present invention is carried out by measuring the force of grasp exerted between the fingers and palm of the hand at a first location near the end of the fingers, at another location near the palm, and at another location between the first and second location. The measured force of grasp at the first, second and third locations are compared to determine the configuration of a curve plotted from the results of the measured force. The shape of the curve determines if the patient is truly exerting a maximum effort while his grasping force is being measured, or whether the patient is not making his maximum effort and therefore the weakness of the grasp can be attributed to this lack of effort rather than to other causes such as muscular weakness and the like.

Accordingly, a primary object of the present invention is the provision of method and apparatus for measuring the power of the grasp of one's hand at a plurality of locations.

Another objection of the invention is to provide a hand held apparatus having movable wall sections that compress a transducer which measures the force of one's grasp.

A further object of this invention is to disclose and provide a transducer device having adjustable movable wall sections arranged to engage predetermined areas of the hand and measure the force of grasp therein.

A still further object of this invention is the provision of a method of evaluating the potential force of grasp exerted by one's hand when the person fails to make his maximum effort during the measurement.

Another and still further object of this invention is the provision of a transducer compressed between the palm and selected areas of the fingers for measuring the force of one's grasp.

An additional object of the present invention is the provision of a system by which a transducer generated signal from a grasp measuring device is treated to provide a method of evaluating the potential force of grasp exerted by one's hand when the person fails to make his maximum effort during the measurement.

These and various other objects and advantages of the invention will become readily apparent to those skilled in the art upon reading the following detailed description and claims and by referring to the accompanying drawings.

The above objects are attained in accordance with the present invention by the provision of a method for use with apparatus fabricated in a manner substantially as described herein.

DETAILED DESCRIPTION OF THE PREFERRED EMBODIMENT

Figure 1:
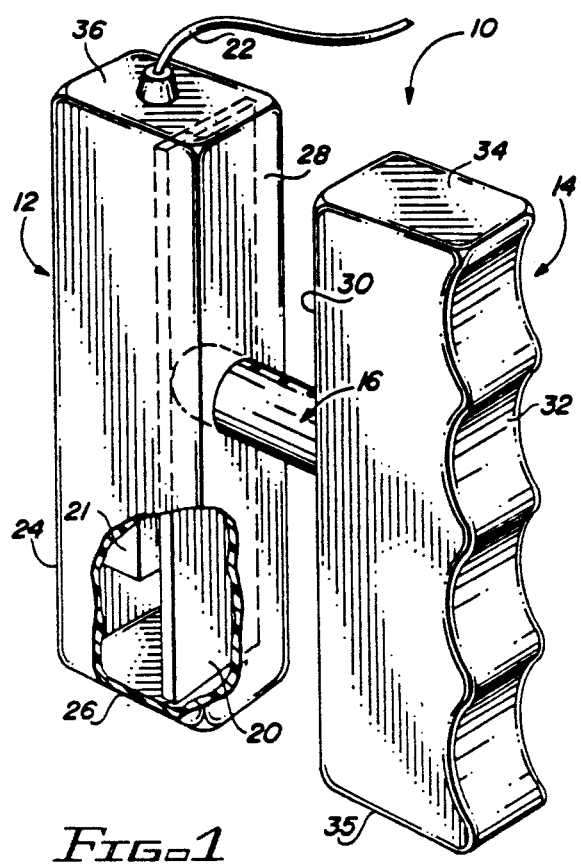
FIG. 1 is a perspective, part cross-sectional view of a grasp analysis apparatus made in accordance with the present invention, with some parts being cut away therefrom in order to disclose the interior thereof.

FIG. 1 of the drawings discloses a grasp analysis apparatus 10 made in accordance with the present invention. The apparatus 10 includes a palm engaging part 12 spaced from a finger engaging part 14 with the palm and finger engaging parts being adjustably held together by a cylindrical shaft 16. The shaft 16 permits the palm engaging part 12 to be moved towards the finger engaging part 14 in direct proportion to the compressive force applied by the hand thereto.

Figure 2:
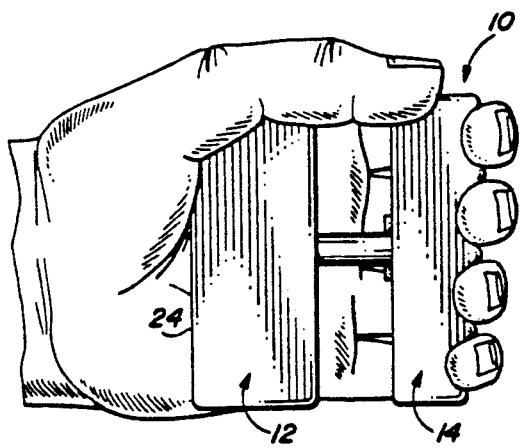
FIG. 2 is a reduced, part schematical, part diagrammatical, top plan view of the apparatus of FIG. 1 shown grasped within one's hand.
Figure 3:
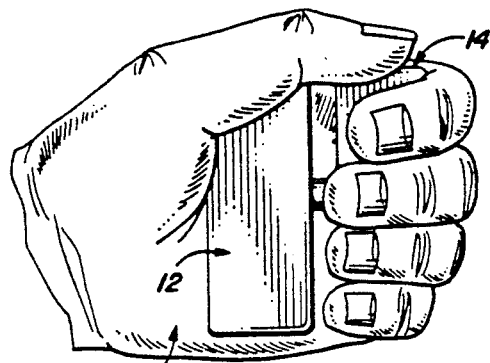
FIG. 3 is similar to FIG. 2 and shows the apparatus in an alternate configuration.
Figure 4:
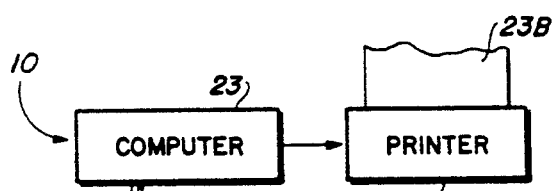
FIG. 4 is a longitudinal, cross-sectional view of the apparatus disclose in FIGS. 1-3.
Figure 4:
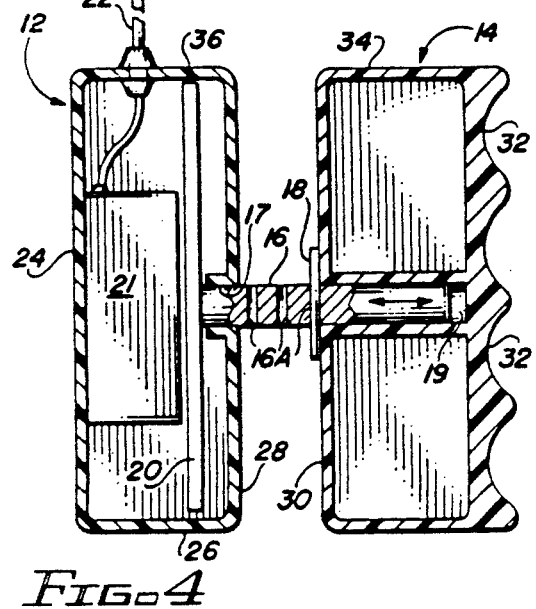

As best seen in FIG. 4, together with FIGS. 1–3, the cylindrical shaft 16 is reciprocatingly received within the illustrated aperture 17. A plurality of drilled holes 16A are formed laterally through shaft 16. Stop member 18, in the form of a pin, is attached to a medial portion of shaft 16 and bears against the finger engaging part 14. Numeral 19 indicates a cylindrical counterbore, preferably open to ambient, for reciprocatingly receiving one marginal end of shaft 16; while the opposed end of shaft 16 is affixed to a movable wall 20. The wall 20 is mounted for movement within the interior of the palm engaging part 12.

Strain gauge or transducer 21 can take on any number of different forms so long as it generates a signal within conductor 22 which is proportional to the grasp force exerted to move the finger engaging part 14 toward the palm engaging part 12.

Computer 23, which can take on a number of different forms, treats the signal at conductor 22 and converts the signal into a measurement that is indicative of the magnitude of the force applied to compress the finger engaging part 14 toward the palm engaging part 12 of the grasp analysis apparatus 10. The converted signal is treated by suitable electronics at 23A to provide a curve at 23B. The apparatus 21, 22, 23, 23A, and 23B therefore is any device that converts the resultant force of the grasp into stored knowledge that is equivalent to the information presented by the curve of FIG. 5.

In FIGS. 1 and 4, the palm engaging part 12 includes the back or rear wall 24, a lower wall 26, and a confronting face 28 that is opposed to the confronting face 30 of the finger engaging part 14. A finger grip 32 is provided for each of the four fingers of the hand. Numeral 34 indicates the top end wall and numeral 35 indicates the bottom end wall of the finger engaging part 14 while numeral 36 indicates a top end wall of the palm engaging part 12.

In FIGS. 6–10, numeral 40 indicates the joinder of the finger to the palm 42. Numeral 44 indicates the end section of the finger. The middle or second section of the finger is indicated by numeral 46, while the first section of the finger is indicated by numeral 48. There is a finger joint between sections 44 and 46, 46 and 48, 48 and 42.

Figure 10:
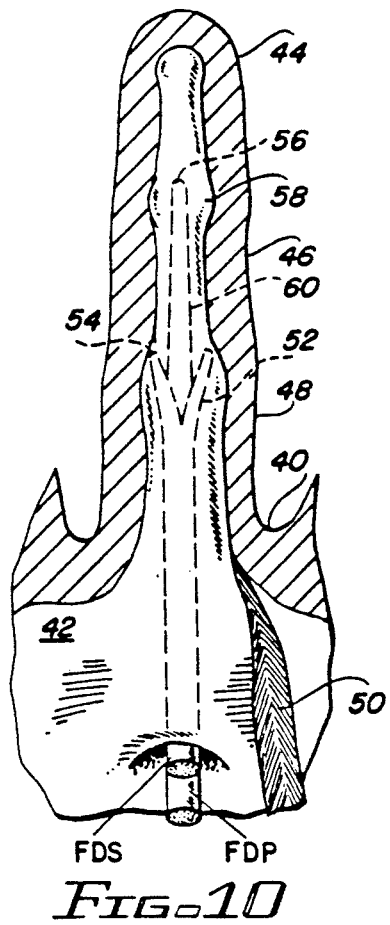

In FIG. 10 the legend FDS is intended to illustrate a flexor digitorum superficialis while the legend FDP indicates a flexor digitorum profundus. Numeral 50 indicates the intrinsic musculature which exerts pressure through the knuckle joint of the finger. Accordingly, there are three groups of muscles brought into play for exerting maximum effect on the power of one's grasp, with the FDP being the first group of muscles, the FDS being the second group of muscles, and the flexor digitorum superficialis tendon being the third group of muscles.

Figure 6:
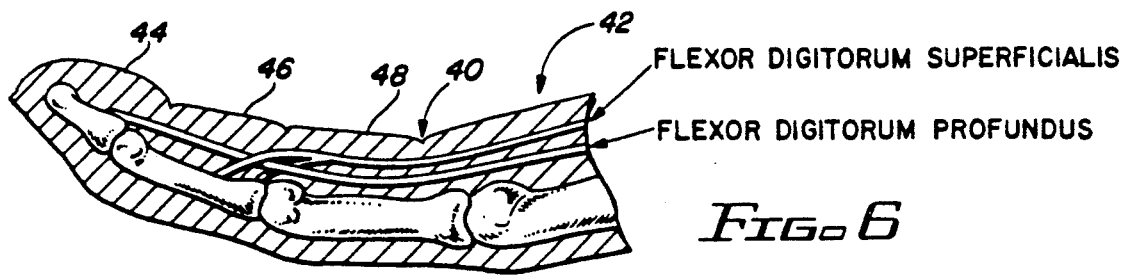
FIG. 6 is diagrammatical, part schematical representation of a human finger.
Figure 7:
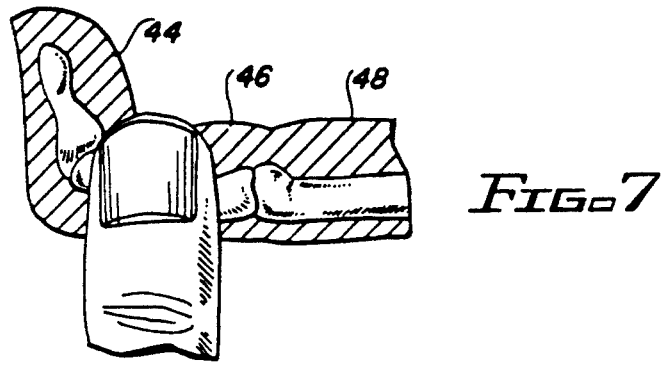
FIG. 7 shows the finger of FIG. 6 in a different configuration.
Figure 8:
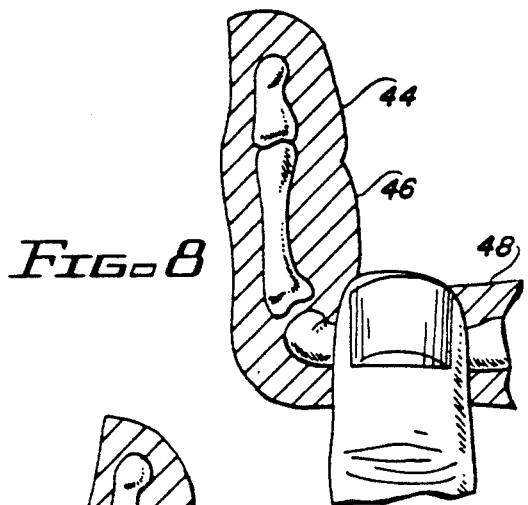
FIG. 8 shows the finger of FIGS. 6 and 7 in a different configuration.
Figure 9:
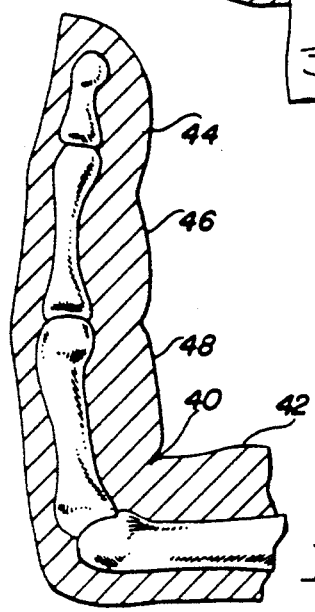
FIG. 9 shows the configuration of the finger of FIGS. 6–8 in another configuration; and, FIG. 10 is a diagrammatical, top, part cross-sectional view of the finger disclosed in FIGS. 6–9.

Numeral 52 of FIG. 10 generally indicates the before mentioned joint located below the location 40 illustrated in FIG. 6; numeral 54 indicates the FDS; numeral 56 indicates the insert of the FDP; numeral 58 indicates the joint between the end and second sections 44 and 46; and numeral 60 indicates a medial part of the FDP.

Figure 5:
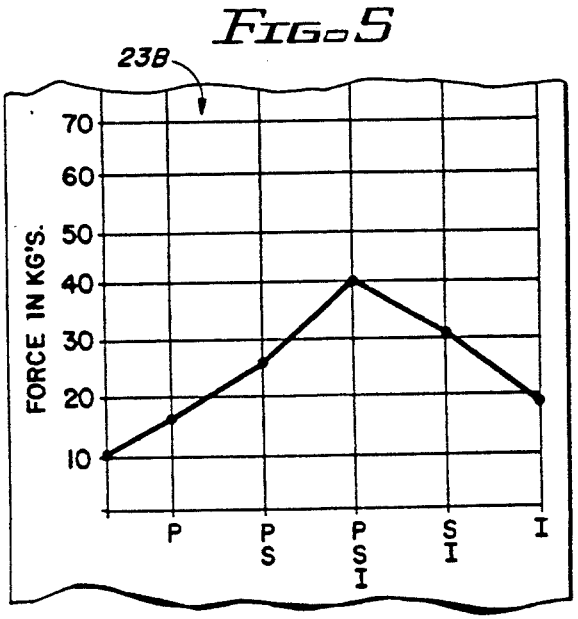
FIG. 5 is a fragmentary, representation of a plot illustrating the method of the present invention.

The palm engaging part 12 of the grasp analysis apparatus 10 of FIGS. 1–4 includes two members, the movable wall 20 and transducer 21, as shown in FIGS. 1 and 4. The transducer 21 is support by the rear wall 24 of the palm engaging part 12. The transducer 21 is activated by the movable wall 20 that moves longitudinally across the chamber as pressure is applied at finger grip 32. The finger engaging part 14 opposite to the palm engaging part 12 comprises a formed member that is contoured as indicated at finger grip 32 to fit the individual fingers so that suitable grasp can be obtained. The cylindrical shaft 16 is adjustably connected thereto which passes out of the housing formed within the finger engaging part 14 and through aperture 17 which freely receives the shaft in a slidable manner. The distance between members 12 and 14 can be easily established by selecting the appropriate hole, of a plurality of holes provided at 16A in shaft 16 through which the stop member 18, in the form of a small pin, is passed. The selected location of this pin respective to shaft 16 will result in a different width between the two members 12 and 14. Thus the appropriate width of the apparatus for each of the five positions along the fingers, as illustrated in the drawings, can be obtained, and the appropriate amount of grip in each of these positions measured by the movable wall 20 compressing and activating the pressure responsive transducer. The results of the measurement obtained with the transducer 21 are then conveyed at conductor 22 into a computer 23 of FIG. 4 which is programmed to create the equivalent of the graph as shown in FIG. 5. Hence the resultant printout 23B in the form of the illustrated curve is the final reading.

The grasp analysis apparatus 10 can be used in a single position in a manner similar to a known or prior art manometer; and, the graph need not be actually drawn so long as data is compiled and presented to achieve the equivalent of stored knowledge, as illustrated by the curve of FIG. 5, for example. However, the grasp analysis apparatus 10 has the capability of creating the grasp analysis curve from which the strength of grasp can be better evaluated in a new and unobvious manner. This capability should be of great advantage to the hand surgeon or the rehabilitationist who must do evaluations of patients with proported impaired hand conditions, and in doing these evaluations one must ascertain whether or not the patient is making maximum effort when his grasp is measured.

Heretofore, there has been no systemized procedure for achieving this desirable goal. The present invention provides a unique method and apparatus for providing this accomplishment.

The grasp analysis apparatus 10 of the present invention is to be used for the measurement of the power of grasp in the human hand, and at the same time evaluate the amount of effort being utilized by the patient for creating the curve as seen in FIG. 5, thus indicating the magnitude of the force of the grasp that is present in certain locations relative to the width of the grasp. When a very wide object, as seen in FIG. 2, for example, is grasped with the hand, only the flexor tendon that attaches distally (the flexor digitorum profundus tendon) acts and this results in a certain amount of pressure being applied to the pressure transducer 21 in the grasp analysis apparatus 10. This is indicated at P on the curve of FIG. 5. With the next smaller grasp width, the flexor digitorum superficialis tendon comes into play since its function is primarily on the middle phalanx of the finger. This is indicated at PS on the curve of FIG. 5. In position three, the function of the profundus, the superficialis is aided by the action of the intrinsic musculature so that all three muscle groups are exerting maximum effect and jointly represent the magnitude of the power of grasp exerted between the palm and fingers. This is indicated at PSI on the curve of FIG. 5. In the next smaller width, or position four, the profundus can mechanically no longer function on this small a width so that the magnitude of the power of graph is produced only by the superficialis tendon 60 and the intrinsics 50. This is indicated at SI on the curve of FIG. 5. Finally, in the smallest width possible, the superficialis and profundus tendons both have become mechanically ineffective because of the smallness of the width between members 12 and 14, and only the intrinsic musculature which exerts pressure through the proximal or knuckle joint 40 of the finger is functional and the reading at 23B will so indicate. This is indicated at I on the curve of FIG. 5.

In analyzing these five locations on the curve of FIG. 5, it will be seen that a bell shaped curve is achieved by plotting normal activity. This configuration of the curve will be evidenced by the data at P, PS, PSI, SI, and I; no matter what strength musculature motivates the hand; and, in most circumstances will be present when the patient is exerting maximum effort at each of the five recited measuring locations. Should the patient, for one reason or another, fail to exert maximum effort, a more straight configuration of curve will result, or a curve that has a downward slant will occur, so that the Examiner realizes that the patient is not making his maximum effort, and therefore the weakness of grasp can be attributed to this lack of effort, rather than to other causes such as muscular weakness and the like. Stated differently, data that results in a curve other than the bell curve of FIG. 5 is a strong indication that the patient is deliberately faking the extent of his injury. The greater the departure of the curve from the bell shaped curve of FIG. 5 is proportional to the degree of the false effort made by the patient.

I claim:

1. A grasp analysis apparatus by which the power of the grasp in the human hand can be measured; said apparatus includes a palm engaging part by which the apparatus is engaged by one's palm, and, a finger engaging part which the fingers can engage and move towards the palm engaging part;
    means connecting said finger engaging part and said palm engaging part to enable the palm engaging part and finger engaging part to be forced toward one another in proportion to the force exerted thereon between the fingers and the palm;
    adjustment means for changing the effective spaced apart distance between said finger engaging part and palm engaging part, and thereby bring various muscle groups of the fingers into use when said palm engaging part and finger engaging part are forced toward one another;
    transducer means responsive to movement between said palm engaging part and finger engaging part for generating a signal which is proportional to the magnitude of the force exerted thereon, and means converting said signal into a measurement indicative of the magnitude of the force.

2. The apparatus of claim 1 wherein said transducer means is connected to a computer means by which said signal provides data representative of the measurement.

3. The apparatus of claim 1 wherein said transducer is a strain gauge; said means connecting is a shaft connected to be reciprocated by relative movement between said palm engaging part and finger engaging part;
    said shaft, when reciprocated, is arranged to engage the strain gauge and thereby generate said signal which is proportional to the magnitude of the force exerted thereon.

4. A grasp analysis apparatus by which the power of the grasp in the human hand can be measured; said apparatus includes a palm engaging part by which the apparatus is engaged by one's palm, and, a finger engaging part which the fingers can engage and move towards the palm engaging part;
    shaft means connecting said finger engaging part and said palm engaging part together to enable the palm engaging part and finger engaging part to be forced toward one another in proportion to the force exerted thereon between the fingers and the palm;
    adjustment means by which the effective length of said shaft means is selected to thereby select the location that the finger engaging part contacts the fingers, which in turn determines the group of muscles that provide the force of grasp jointly exerted between the fingers and palm of the hand;
    transducer means responsive to movement between said palm engaging part and finger engaging part for generating a signal which is proportional to the magnitude of the force exerted thereon, and means converting said signal into a measurement indicative of the magnitude of the force.

5. The apparatus of claim 4, wherein a moving wall member is attached to said shaft means and engages the transducer means, said transducer means is strain gauge which measures the magnitude of the force of grasp.

6. Apparatus of a size to be grasped in the hand for use in evaluating the force of grasp one can exert with a hand and to thereby determine when less than the maximum force is actually being exerted;
    said apparatus comprising a palm engaging part, a finger engaging part spaced from said palm engaging part, shaft means extending between said finger engaging part and said palm engaging part;
    adjustment means for changing the effective length of said shaft means; a transducer for changing the force of grasp into data; said shaft means engages said transducer with an applied force that is proportional to the force of grasp exerted on said finger engaging part and said palm engaging part;
    said adjustment means enable the force of grasp jointly exerted between the fingers and palm of the hand to be applied at different locations along the fingers when the space between said finger engaging part and said palm engaging part is changed;

means comparing the measured force of grasp at said different locations to determine the configuration of a curve plotted from said measured force;

whereby, data related to a bell shaped curve is provided with a high degree of confidence while data related to a curve other than a bell shaped curve is provided with a low degree of confidence which is considered a false representation of ones effort.

7. The apparatus of claim 6 wherein the force of grasp in measured at a plurality of different positions between the palm engaging part and the finger engaging part by changing the effective length of the shaft means an amount wherein the action of three groups of muscles is effected on the transducer as follows: the flexor digitorum profundus, flexor digitorum superficialis, and the flexor digitorum superficialis tendon.

8. The apparatus of claim 6 wherein one of said finger engaging part and palm engaging part is in the form of a housing having opposed walls, said transducer is mounted within said opposed walls, said opposed walls are compressed towards one another when said finger engaging part and said palm engaging part is grasped between the palm and fingers to thereby provide a signal proportional to the force of the grasp; and, means including said transducer for converting the signal into data that is related to said curve.

9. The apparatus of claim 8 wherein the action of three groups of muscles is effected on the transducer as follows: the flexor digitorum profundus, flexor digitorum superficialis, and the flexor digitorum superficialis tendon.

10. The apparatus of claim 6, wherein the transducer is placed within a housing having opposed walls which are compressed towards one another when the apparatus is grasped between the palm and fingers to thereby provide a signal proportional to the force of the grasp; and, means converting the signal into data that is related to said curve and wherein said transducer obtains different measuring forces between the locations on the fingers engaging part by changing the effective length of the shaft an amount wherein the action of three groups of muscles is effected on the transducer as follows: the flexor digitorum profundus, flexor digitorum superficialis, and the flexor digitorum superficialis tendon.

11. Apparatus by which the force of grasp one exerts with a hand is measured to determine when less than the maximum force is actually being exerted, comprising:

a palm engaging part, a finger engaging part spaced from said palm engaging part, shaft means extending between said finger engaging part and said palm engaging part and mounted to reciprocate respective to one of said finger engaging part and said palm engaging part;

adjustment means for changing the effective length of said shaft means; a transducer mounted respective to the other of said finger engaging part and said palm engaging part; said shaft means engages said transducer with an applied force that is proportional to the force of grasp exerted on said finger engaging part and said palm engaging part;

means including said transducer for measuring the force of grasp jointly exerted between the fingers and palm of the hand at a first location near the end of the fingers; means including said transducer for measuring the force of grasp jointly exerted between the fingers and palm of the hand at another location that is near the palm; and means including said transducer for measuring the force of grasp jointly exerted between the fingers and palm of the hand at a third location between said first and second location;

means comparing the measured force of grasp at said first, second and third locations to determine the configuration of a curve plotted from said measured force;

means constructing a curve and for comparing the resultant curve to a bell shaped curve which is considered a true representation of ones effort; while a curve other than a bell shaped curve is considered as a false representation of ones effort to grasp an object.

12. The apparatus of claim 11 wherein the force of grasp is measured at various different locations along the fingers that include various combinations of the flexor digitorum profundus, flexor digitorum superficialis, and the flexor digitorum superficialis tendon; and means plotting the resultant data to provide indicia related to said curve.

13. The apparatus of claim 12 and further including mounting said transducer within a housing having opposed walls which are compressed towards one another when said apparatus is grasped between the palm and fingers to provide a signal proportional to the force of the grasp; and, means converting the signal into data that is related to said curve.

14. The apparatus of claim 11 wherein the length of said shaft means is adjustable to provide various different selected widths of the apparatus so that the force applied at the recited locations of the finger engaging part is effected by the action of three groups of muscles, as follows: the flexor digitorum profundus, flexor digitorum superficialis, and the flexor digitorum superficialis tendon.

* * * * *